(12) United States Patent
Lee et al.

(10) Patent No.: US 12,414,734 B2
(45) Date of Patent: Sep. 16, 2025

(54) ELECTRONIC DEVICE AND METHOD FOR DIAGNOSING DEMENTIA WITH LEWY BODIES OR PREDICTING MORBIDITY TO DEMENTIA WITH LEWY BODIES

(71) Applicant: Seoul National University R&DB Foundation, Seoul (KR)

(72) Inventors: Jee Young Lee, Seoul (KR); Hee Jung Kim, Gwangju-Si (KR); Jung Hwan Shin, Seoul (KR); Yu Kyeong Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 140 days.

(21) Appl. No.: 18/230,352

(22) Filed: Aug. 4, 2023

(65) Prior Publication Data
US 2024/0041387 A1 Feb. 8, 2024

(30) Foreign Application Priority Data
Aug. 5, 2022 (KR) .................. 10-2022-0098189

(51) Int. Cl.
*A61B 5/00* (2006.01)
*A61B 5/055* (2006.01)
(52) U.S. Cl.
CPC .......... *A61B 5/4088* (2013.01); *A61B 5/055* (2013.01); *A61B 5/7246* (2013.01); *A61B 5/7275* (2013.01)
(58) Field of Classification Search
CPC ..... A61B 5/4088; A61B 5/055; A61B 5/7246; A61B 5/7275; A61B 5/107; A61B 2576/026; A61B 5/4082; A61B 5/0042; A61B 5/4064; A61B 2503/08; G01R 33/5608; G06T 7/0012; G16H 30/40; G16H 50/20; G16H 50/30; G16H 50/50
See application file for complete search history.

(56) References Cited

U.S. PATENT DOCUMENTS

| | | |
|---|---|---|
| 2016/0300352 A1* | 10/2016 | Raj ..................... G06V 10/764 |
| 2020/0027557 A1 | 1/2020 | Karow et al. |
| 2020/0241011 A1* | 7/2020 | Kaddurah-Daouk ...................... A61B 5/4088 |

FOREIGN PATENT DOCUMENTS

KR  10-2020-0062589 A  6/2020

OTHER PUBLICATIONS

Office Action issued in counterpart Korean Patent Application No. 10-2022-0098189 A, mailed Mar. 19, 2024 (6 pages).

(Continued)

*Primary Examiner* — Bo Joseph Peng
(74) *Attorney, Agent, or Firm* — Osha Bergman Watanabe & Burton LLP (57) ABSTRACT

The electronic device for diagnosing dementia with Lewy bodies (DLB) or predicting morbidity to DLB according to the present invention includes a processor that measures cortical thicknesses for a plurality of regions of the brain by using brain MRI images of a normal group and a DLB patient group, generates a DLB pattern matrix by using a residual matrix according to a difference between the average cortical thickness and the cortical thickness for each region, applies a first cortical thickness matrix generated by using a brain MRI image of the subject to the DLB pattern to calculate a first DLB pattern score, and diagnoses the subject as DLB or predicting morbidity to DLB by using the first DLB pattern score.

19 Claims, 7 Drawing Sheets

(56) References Cited

OTHER PUBLICATIONS

R. Ye, et al. "Topography of cortical thinning in the Lewy body diseases." NeuroImage: Clinical 26 (2020) 102196, pp. 1-11 (11 pages).
Colloby, et al. "Multivariate spatial covariance analysis of 99mTc-exametazime SPECT images in dementia with Lewy bodies and Alzheimer's disease: utility in differential diagnosis." Journal of Cerebral Blood Flow & Metabolism (2013), pp. 612-618 (7 pages).
Shin et al. "Multimodal imaging stratifies subtype-specific disease conversion in isolated REM-sleep behavior disorder." Department of Neurology, Seoul Metropolitan Government-Seoul National University Boramae Medical Center , Seoul, Korea, Republic of. (3 pages).

* cited by examiner

ELECTRONIC DEVICE AND METHOD FOR DIAGNOSING DEMENTIA WITH LEWY BODIES OR PREDICTING MORBIDITY TO DEMENTIA WITH LEWY BODIES

CROSS-REFERENCE TO RELATED APPLICATION

This application claims priority to and the benefit of Korean Patent Application No. 10-2022-0098189, filed on Aug. 5, 2022, the disclosure of which is incorporated herein by reference in its entirety.

TECHNICAL FIELD

The present invention relates to an electronic device and method for diagnosing dementia with Lewy bodies or predicting morbidity to dementia with Lewy bodies.

BACKGROUND ART

Dementia is a disease in which both the incidence and morbidity are increasing due to an increase in the elderly population, and it is a disease that greatly affects death, a decrease in the quality of life and social and economic burdens for the elderly population. Currently, attempts have been made to develop a disease-modifying treatment for dementia that can change the course of the disease, such as stopping or slowing the progression of the disease, but the situation is that none of the drugs have been commercialized yet with sufficient evidence of effectiveness.

In neurodegenerative diseases such as dementia, the degeneration of nerve cells in the brain is already quite advanced at the time when symptoms appear and diagnosis is made, and thus, it is already too late to prevent the degeneration of nerve cells with interventional therapy. Therefore, opinions have been raised in the academic world that a therapeutic agent must be developed from the prodromal stage before the onset of the disease.

Dementia with Lewy bodies is the second most common neurodegenerative disease after Alzheimer's dementia, and dementia with Lewy bodies goes through a prodromal stage of up to 10 years before dementia appears, and among various prodromal stages, REM sleep behavior disorder is the prodromal symptom with the highest diagnostic specificity.

REM sleep behavior disorder is a precursor to not only dementia with Lewy bodies but also Parkinson's disease, which pathologically has the same Lewy bodies but has a different progression. Since the clinical symptoms of dementia with Lewy bodies and Parkinson's disease are different, the method for determining disease progression must be different, and particularly, when developing a therapeutic agent in the prodromal stage, efficacy indicators must be calculated by differentiating the two diseases such that disease progression can be appropriately monitored. Therefore, it is very important differentiate whether to progress to dementia with Lewy bodies or Parkinson's disease in the future at the stage of REM sleep behavior disorder.

Among the various markers developed for REM sleep behavior disorder, there are currently no markers that have been proven to differentiate between prodromal-stage dementia with Lewy bodies and Parkinson's disease, and currently, dementia is diagnosed and differentiated clinically through tests such as symptoms and imaging. However, Alzheimer's dementia and dementia with Lewy bodies, which are major degenerative dementias, are often difficult to differentiate based on symptoms, magnetic resonance imaging (MRI) or amyloid images alone in mild cognitive impairment, which is a prodromal stage. Imaging tests that can be used in the prodromal stage include brain MRI, brain MG PET (Fluorodeoxyglucose positron emission tomography), DAT PET (Dopamine transporter positron emission tomography) and the like, but the situation is that a systematic prospective cohort study is needed to find out what valid clinical information each imaging test provides in REM sleep behavior disorder, which is a prodromal stage to dementia with Lewy bodies. In particular, the analysis of large-scale cohort data using DAT images is in progress, but this is data using the SPECT (Single Photon Emission Computed. Tomography) technique, and the sensitivity and specificity are poor due to poor spatial resolution like PET, and it has a disadvantage in that it is difficult to utilize in the domestic situation where the PET images are mostly taken. A large-scale cohort study has not yet been conducted for FDG PET, and there is no prospective data for MRI.

In addition, the fluorodeoxyglucose (FDG) and dopamine transporter (DAT) imaging-based biomarkers that have been proposed so far are helpful in predicting progression to Lewy body disease in patients with REM sleep behavior disorder, but it is known that it is difficult to predict and differentiating between dementia with Lewy bodies and Parkinson's disease among Lewy body diseases.

As a related art associated with dementia diagnosis using brain MRI images, Korean Patent. Application Laid-Open No. 10-2020-0062589 discloses a device and method for predicting dementia through the segmentation of brain MRI images by brain region, but by applying the measured brain capacity for each region to a deep learning model, it only predicts the probability of developing dementia for each brain region and the time when the subject may develop dementia, and no mention has been made of a technique for diagnosing whether to progress from REM sleep behavior disorder to dementia with Lewy bodies or to Parkinson's disease.

Under this background, the inventors of the present invention have made diligent efforts to develop an objective image index that can predict the progression to dementia with Lewy bodies from the prodromal stage with high reliability, and as a result, the present invention was completed by developing an algorithm for obtaining a brain spatial covariance network pattern of the thickness of the brain cortex of patients with dementia with Lewy bodies by applying SSM-PCA (Scaled Subprofile Model, Principal Component Analysis) using the 3D T1 sequence obtained from 3T MRI as an analysis material and providing a diagnosis technique that differentiates between dementia with Lewy bodies and Parkinson's disease in the prodromal stage based on the ULB pattern standard score derived through the corresponding algorithm.

DISCLOSURE

Technical Problem

An object of the present invention is to provide an electronic device and method for diagnosing dementia with Lewy bodies and predicting morbidity to dementia with Lewy bodies, which can predict the progression of disease with high reliability by differentiating patients with dementia with Lewy bodies and Parkinson's disease from the prodromal stage.

Another object of the present invention is to provide an electronic device and method for diagnosing dementia with Lewy bodies or predicting morbidity to dementia with Lewy bodies, which are more accessible and have high reproducibility in repeated measurements.

Technical Solution

The electronic device for diagnosing dementia with Lewy bodies (DLB) or predicting morbidity to DLB includes a processor for measuring cortical thicknesses for a plurality of regions of the brain by using brain MRI images of a normal group and a DLB patient group, generating a DLB pattern matrix by using a residual matrix according to a difference between the average cortical thickness and the cortical thickness for each region, applying a first cortical thickness matrix generated by using a brain MRI image of a subject to the DLB pattern to calculate a first DLB pattern score, and diagnosing the subject as DLB or predicting morbidity to DLB by using the first DLB pattern score.

The processor may generate a covariance matrix representing a correlation between cortical thicknesses for each region by using the residual matrix, and generate the DLB pattern matrix according to at least one principal component of the covariance matrix extracted through principal component analysis.

The processor may identify a DLB pattern matrix having the lowest Akaike information criterion value among a plurality of DLB pattern matrices generated based on different principal components.

The processor may measure cortical thicknesses for a plurality of regions of the brain by using a brain MRI image of the subject, and generate the first cortical thickness matrix including the cortical thickness for each region.

The processor may generate a plurality of cortical thickness matrices including cortical thicknesses for each region of the normal group and the DLB patient group, and generate the residual matrix by using the plurality of cortical thickness matrices.

The processor may calculate the first DLB pattern score as a standard score compared to the distribution of DLB pattern scores in the normal group to diagnose the subject as DLB or predict morbidity to DLB.

The age and gender of the subject may be matched in the normal group.

The processor may differentiate the subject from Parkinson's disease based on whether a cut-off value of the standard score is exceeded to diagnose the subject as DLB or predict morbidity to DLB.

The processor may diagnose the subject as DLB or predict that the subject is afflicted with DLB, if the standard score is more than the cut-off value, and predicts that the subject is afflicted with Parkinson's disease, if the standard score is less than or equal to the cut-off value.

The processor may predict that the subject's memory and spatial perception ability are reduced, if the subject is a REM sleep behavior disorder patient and the standard score is more than the cut-off value.

The cut-off value may be 1.

The method for diagnosing dementia with Lewy bodies (DLB) or predicting morbidity to DLB which is performed by a device for diagnosing DLB or predicting morbidity to DLB according to an exemplary embodiment of the present invention includes the steps of measuring cortical thicknesses for a plurality of regions of the brain by using brain MRI images of a normal group and a DLB patient group; generating a DLB pattern matrix by using a residual matrix according to a difference between the average cortical thickness and the cortical thickness for each region; calculating a first DLB pattern score by applying a first cortical thickness matrix generated by using a brain MRI image of a subject to the DLB pattern matrix; and diagnosing the subject as DLB or predicting morbidity to DLB by using the first DLB pattern score.

The step of generating a DLB pattern matrix may include the steps of generating a covariance matrix representing a correlation between cortical thicknesses for each region by using the residual matrix; and generating the DLB pattern matrix according to at least one principal component of the covariance matrix extracted through principal component analysis.

The step of generating a DLB pattern matrix may include the step of identifying a DLB pattern matrix having the lowest Akaike information criterion value among a plurality of DLB pattern matrices generated based on different principal components.

The step of calculating a first DLB pattern score may include the steps of: measuring cortical thicknesses for a plurality of regions of the brain by using a brain MRI image of the object; and generating the first cortical thickness matrix including the cortical thickness for each region.

The step of generating a DLB pattern matrix comprises the steps of generating a plurality of cortical thickness matrices including cortical thicknesses for each region of the normal group and the DLB patient group; and generating the residual matrix by using the plurality of cortical thickness matrices.

The step of diagnosing the subject as DLB or predicting morbidity to DLB comprises the step of diagnosing the subject as DLB or predicting morbidity to DLB by calculating the first DLB pattern score as a standard score compared to the distribution of DLB pattern scores in the normal group.

The step of diagnosing the subject as DLB or predicting morbidity to DLB comprises the step of diagnosing the subject as DLB or predicting morbidity to DLB based on whether the cut-off value of the standard score is exceeded.

The step of diagnosing the subject as DLB or predicting morbidity to DLB may include the steps of diagnosing the subject as DLB or predicting that the subject is afflicted with DLB, if the standard score is more than the cut-off value; and predicting that the subject is afflicted with Parkinson's disease, if the standard score is less than or equal to the cut-off value.

The method may further include the step of determining that the subject's memory and spatial perception ability are reduced, if the subject is a REM sleep behavior disorder patient and the standard score is more than the cut-off value.

The method may further include the step of combining with at least one selected from the group consisting of a clinical biomarker, an imaging biomarker and a blood biomarker of the subject to predict whether the subject has developed DLB or is afflicted with DLB.

Advantageous Effects

According to an exemplary embodiment of the present invention, it is possible to predict disease progression by differentiating patients with dementia with Lewy bodies and Parkinson's disease from the prodromal stage with high reliability.

According to an exemplary embodiment of the present invention, it is possible to provide an electronic device for diagnosing DLB or predicting morbidity to DLB with high applicability and reproducibility by determining whether a disease progresses by using only a brain MRI image of a subject.

According to an exemplary embodiment of the present invention, it is possible to provide a biomarker that prioritizes objectivity and reproducibility in differentiating patients with prodromal-stage dementia with Lewy bodies and Parkinson's disease while taking into account individual differences in the brain within an anatomical space.

MODES OF THE INVENTION

Hereinafter, preferred exemplary embodiments according to the present invention will be described in detail with reference to the accompanying drawings. The detailed description set forth below in conjunction with the accompanying drawings is intended to describe the exemplary embodiments of the present invention and is not intended to represent the only exemplary embodiments in which the present invention may be practiced. In order to clearly describe the present invention in the drawings, parts that are irrelevant to the description may be omitted, and the same reference numerals may be used for the same or similar components throughout the specification. Further, in the exemplary embodiments of the present invention, terms including ordinal numbers such as first and second are used only for the purpose of distinguishing one component from another component, and singular expressions include plural expressions unless the context clearly dictates otherwise.

Figure 1:
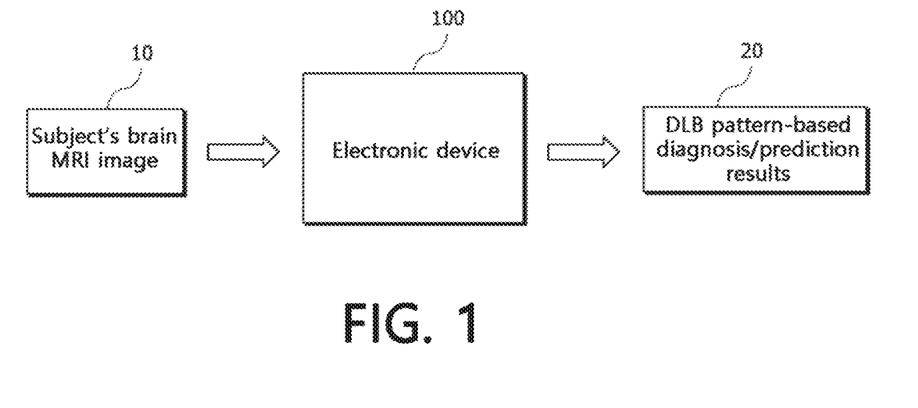
FIG. 1 is a diagram schematically illustrating the method for diagnosing dementia with Lewy bodies or predicting morbidity to dementia with Lewy bodies according to an exemplary embodiment of the present invention.

FIG. 1 is a diagram schematically illustrating the method for diagnosing dementia with Lewy bodies or predicting morbidity to dementia with Lewy bodies according to an exemplary embodiment of the present invention.

FIG. 1 illustrates an electronic device 100 for diagnosing DLB or predicting morbidity to DLB (hereinafter, referred to as an electronic device 100), a brain MRI image of a subject that is input to the electronic device 100, and diagnosis/prediction results based on a DLB pattern that is output through the electronic device 100.

The electronic device 100 according to an exemplary embodiment of the present invention is a device for outputting a prediction result 20 of diagnosing DLB or predicting morbidity to DLB of a subject by applying the brain MRI image 10 of the subject into a spatial covariance network pattern (hereinafter, referred to as a DLB pattern) of cortical thicknesses that are specific to dementia with Lewy bodies (hereinafter, also referred to as DLB), and it may be implemented as a computer, server or the like.

According to an exemplary embodiment of the present invention, the DLB pattern may be used as a biomarker that can be used to predict a future onset of dementia in a subject and differentiate between dementia with Lewy bodies and Parkinson's disease.

The subject includes a non-patient, a prodromal-stage dementia patient and a dementia patient, and the subject's brain MRI image 10 may be a 3 Teslar(T) MRI 3D sequence that is widely used in clinical settings.

The electronic device 100 according to an exemplary embodiment of the present invention performs an algorithm for extracting a DLB pattern, and uses the brain MRI image 10 of the subject to indicate how close the cortical thickness pattern of the subject is to the DLB pattern as a score.

The electronic device 100 may output a prediction result 20 of whether the disease of the subject will progress to DLB in the future through the identified score.

According to an exemplary embodiment of the present invention, an integrated data analysis algorithm for detecting structural changes in the brain in the relationship between the entire brain regions in an anatomical space is proposed. Therefore, it is possible to provide an indicator that measures and indicates structural changes in the brain as an objective and quantitative indicator that excludes the subjectivity of an interpreter. Hereinafter, the configuration and operation of the electronic device 100 according to an exemplary embodiment of the present invention will be described in more detail with reference to the drawings.

Figure 2:
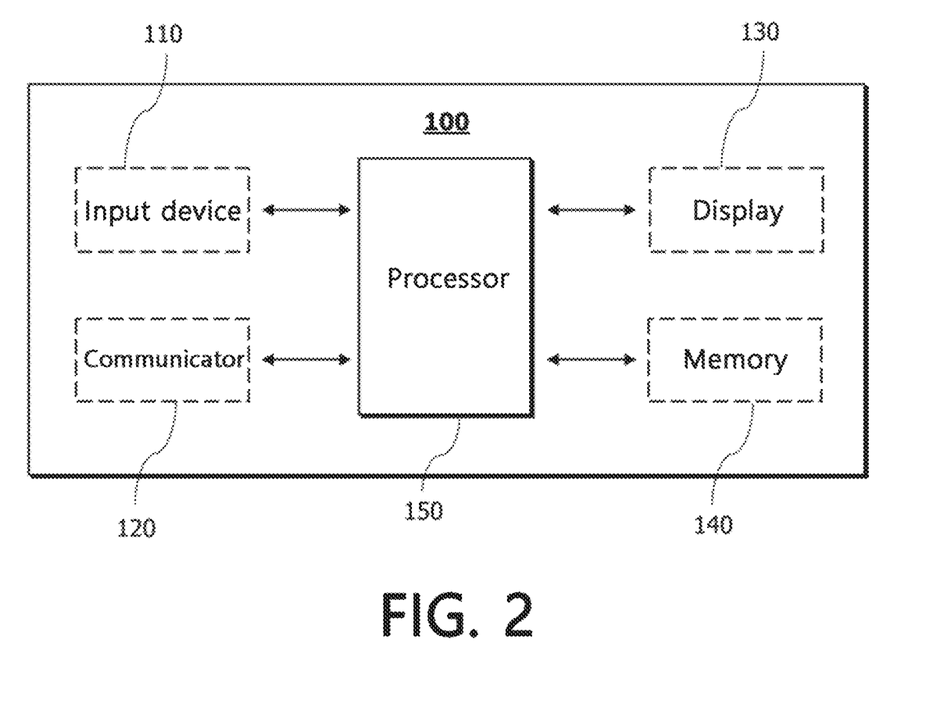
FIG. 2 is a block diagram illustrating the configuration of an electronic device for diagnosing dementia with Lewy bodies or predicting morbidity to dementia with Lewy bodies according to an exemplary embodiment of the present invention.

FIG. 2 is a block diagram illustrating the configuration of an electronic device for diagnosing dementia with Lewy bodies or predicting morbidity to dementia with Lewy bodies according to an exemplary embodiment of the present invention.

The electronic device 100 according to an exemplary embodiment of the present invention includes an input device 110, a communicator 120, a display 130, a memory 140 and a processor 150.

The input device 110 generates input data in response to a user input of the electronic device 100. For example, the user input may be a user input that starts the operation of the electronic device 100, and it is applicable without limitation to a user input that is necessary for diagnosing DLB or predicting morbidity to DLB of a subject.

The input device 110 includes at least one input means. The input device 110 may include a keyboard, a key pad, a dome switch, a touch panel, a touch key, a mouse, a menu button and the like.

The communicator 120 communicates with external devices such as MRI equipment and servers in order to receive brain MRI images. To this end, the communicator 120 may perform communication such as 5th generation communication (5G), long term evolution-advanced (LTE-A), long term evolution (LTE), and (Wi-Fi) and the like.

The display 130 displays display data according to the operation of the electronic device 100. The display 130 includes a screen for displaying a brain MRI image of a subject, a screen for displaying a first cortical thickness matrix that is acquired by using the brain MRI image of a subject, a screen for displaying diagnosis/prediction results, a screen for receiving a user input and the like.

The display 130 may include a liquid crystal display (LCD), a light emitting diode (LED) display, an organic LED (OLED) display, a micro-electro mechanical systems (MEMS) display and an electronic paper display. The display 130 may be combined with the input device 110 and implemented as a touch screen.

The memory 140 stores operating programs of the electronic device 100. The memory 140 includes a non-volatile storage that can retain data (information) regardless of whether electric power is provided, a volatile memory which can load data to be processed by the processor 150 and cannot preserve data if electric power is not provided. Examples of the storage include flash-memory, hard-disc drive (HDD), solid-state drive (SSD), read-only memory (ROM) and the like, and examples of the memory include buffer, random access memory (RAM) and the like.

The memory 140 may store a brain MRI image received from an external device, generate a cortical thickness matrix through a brain MRI image or store an arithmetic program that is necessary for calculating DLB pattern scores and standard scores.

The processor 150 may execute software such as a program to control at least one other component (e.g., a hardware or software component) of the electronic device 100 and perform various data processing or calculations. According to an exemplary embodiment, the processor 150 may include a main processor serving as a central processing unit (CPU) or an application processor and a graphic processing unit (GPU) that can be operated independently or together with the main processor.

The processor 150 measures cortical thicknesses for a plurality of regions of the brain by using the brain MRI images of the normal group and the DLB patient group, generates a DLB pattern matrix by using a residual matrix according to a difference between the average cortical thickness and the cortical thickness for each region, calculates a first DLB pattern score by applying the first cortical thickness matrix generated by using the brain MRI image of the subject to the DLB pattern matrix, and uses the first DLB pattern score to diagnose the subject as DLB or predict morbidity to DLB.

Meanwhile, the processor 150 may perform at least some of the data analysis, processing and result information generation for performing the above operations by using at least one of machine learning, neural network or deep learning as a rule-based or artificial intelligence algorithm. Examples of the neural network may include models such as a convolutional neural network (CNN), a deep neural network (DNN) and a recurrent neural network (RNN).

Figure 3:
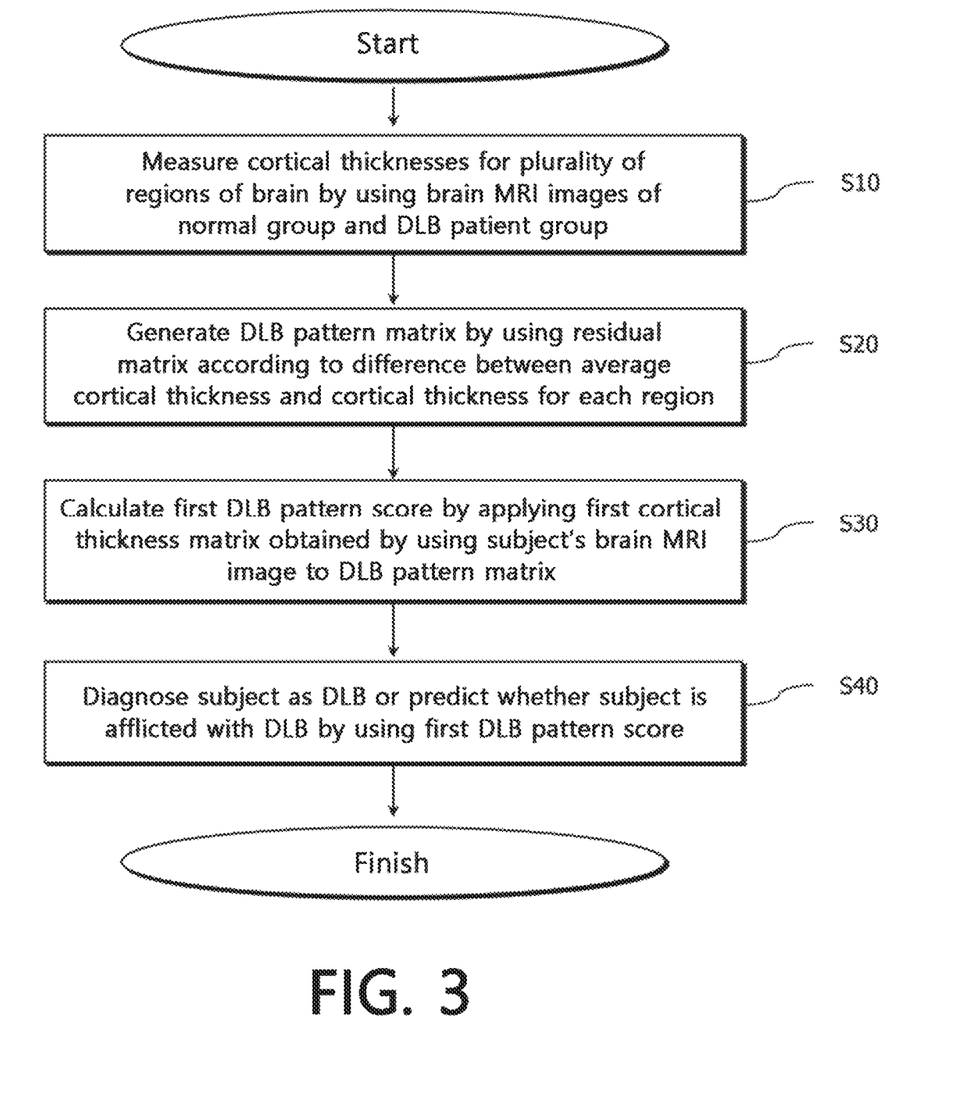
FIG. 3 is a diagram illustrating the operation flowchart of an electronic device according to an exemplary embodiment of the present invention.

FIG. 3 is a diagram illustrating the operation flowchart of a device for predicting dementia with Lewy bodies according to an exemplary embodiment of the present invention.

According to an exemplary embodiment of the present invention, the processor 150 measures cortical thicknesses for a plurality of regions of the brain by using brain MRI images of the normal group and the DLB patient group (S10).

According to an exemplary embodiment of the present invention, the normal group includes a plurality of non-patients, that is, subjects who do not have DLB or REM sleep behavior disorder, which is a prodromal stage thereof, and the DLB patient group includes a plurality of patients who are diagnosed with dementia with Lewy bodies. In this case, the ages of the normal group and the DLB patient group may be matched. According to an exemplary embodiment of the present invention, the processor 150 may more clearly extract the specific brain cortical thickness pattern of the DLB patient by comparing the brain cortical thicknesses of the normal group and the DLB patient group.

The brain MRI image according to an exemplary embodiment of the present invention is an image captured by 3D MRI targeting the entire brain region, and it may refer to an image that is acquired through image standardization and preprocessing. The brain MRI image may be an image having the following properties: 224 slices, TR=9.9 ms, TE=4.6 ms, slice thickness=1 mm, flip angle=8°, FOV=220×220 mm, but the present invention is not limited thereto.

The processor 150 may receive brain MRI images of the normal group and the DLB patient group from the MRI equipment or through the server through the communicator 120.

According to an exemplary embodiment of the present invention, the processor 150 may measure cortical thicknesses ro4 a plurality of regions of the brain through standardized and preprocessed brain MRI images of the normal group and the DLB patient group. For example, the processor 150 may divide the brain into 148 brain regions for each individual and measure the cortical thickness of each region. In this case, each region of the brain is also referred to as a region of interest (ROI) region. The processor 150 may use Freesurfer software, AAL3 atlas and the like in the process of measuring brain cortical thickness.

According to an exemplary embodiment of the present invention, the processor 150 generates a DLB pattern matrix by using a residual matrix according to a difference between the average cortical thickness and the cortical thickness for each region (S20).

The processor 150 may generate a cortical thickness matrix including the cortical thickness for each region obtained for each individual, and generate a residual matrix including residuals according to a difference between the average cortical thickness for each individual and the cortical thickness for each region.

In this case, the processor 150 may generate a plurality of cortical thickness matrices including cortical thicknesses for each region of the normal group and the DLB patient group, and generate a residual matrix by using the plurality of cortical thickness matrices. Hereinafter, unless otherwise mentioned in the description, the residual matrix is determined to mean the residual matrices of the entire normal group and the DLB patient group. For example, the residual matrices for 148 brain regions of a normal group (n=44) and a DLB patient group (n=22) may have a size of 66*148 or 148*66.

The processor 150 may generate a DLB pattern matrix by using a residual matrix of the normal group and the DLB patient group.

The DLB pattern matrix represents a pattern of the specific cortical thickness of a DLB patient obtained by analyzing a difference in cortical thicknesses between the normal group and the DLB patient group, that is, a DLB pattern as a matrix. The DLB pattern matrix consists of a single matrix for brain cortical thickness. Further details of generating the DLB pattern matrix will be described with reference to FIG. 4.

According to an exemplary embodiment of the present invention, the processor 150 calculates a first DLB pattern score by applying the first cortical thickness matrix generated by using a brain MRI image of a subject to a DLB pattern matrix (S30).

The subject according to an exemplary embodiment of the present invention is a subject whose progression to DLB is to be predicted in the future, and the brain MRI image of a subject refers to an image on which image standardization and preprocessing have been performed.

The processor 150 may measure cortical thicknesses for a plurality of regions of the brain by using a brain MRI image of the subject, and generate a first cortical thickness matrix including cortical thicknesses for each region.

The processor 150 calculates a first DLB pattern score by applying the first cortical thickness matrix to the DLB pattern matrix generated in S20.

More specifically, the processor 150 may calculate a first DLB pattern score, which is a single score, by multiplying the first cortical thickness matrix of the subject and the DLB pattern matrix. As described above, since the DLB pattern matrix consists of a single matrix for brain cortical thickness, it can be considered that weight is given to the first cortical thickness matrix.

According to an exemplary embodiment of the present invention, the processor 150 diagnoses the subject as DLB or predicts morbidity to DLB by using the first DLB pattern score (S40).

The DLB pattern score may be used to ascertain how close the subject's cortical thickness pattern is to the DLB pattern. More specifically, the processor 150 may calculate the first DLB pattern score as a z-score compared to the distribution of DLB pattern scores of the normal group. In this case, the normal group is characterized in that the age and gender of the subject are matched.

According to an exemplary embodiment of the present invention, it is possible to diagnose a subject as DLB or predict morbidity to DLB by using a standard score corresponding to the first DLB pattern score.

More specifically, the processor 150 may differentiate the subject from Parkinson's disease based on whether the standard score is more than a cut-off value, diagnose the subject as DLB or predict morbidity to DLB.

For example, the processor 150 diagnoses the subject as DLB or predicts that the subject's disease is afflicted with DLB, if the standard score is more than a cut-off value, and if the standard score is less than or equal to the cut-off value, it can be predicted that the subject's disease will be afflicted with Parkinson's disease. In this case, the cutoff value may be 1.

Hereinafter, more specific information for diagnosing DLB or predicting morbidity to DLB will be described with reference to FIG. 6.

According to an exemplary embodiment of the present invention, since the results do not vary depending on voxelization or parcellation of the brain, it is possible to provide a highly reliable and objective indicator of the progression of the disease to DLB or Parkinson's disease.

According to an exemplary embodiment of the present invention, it is possible to provide an electronic device having high applicability and high reproducibility, because it determines the progression of disease by using only a brain MRI image of a subject.

Figure 4:
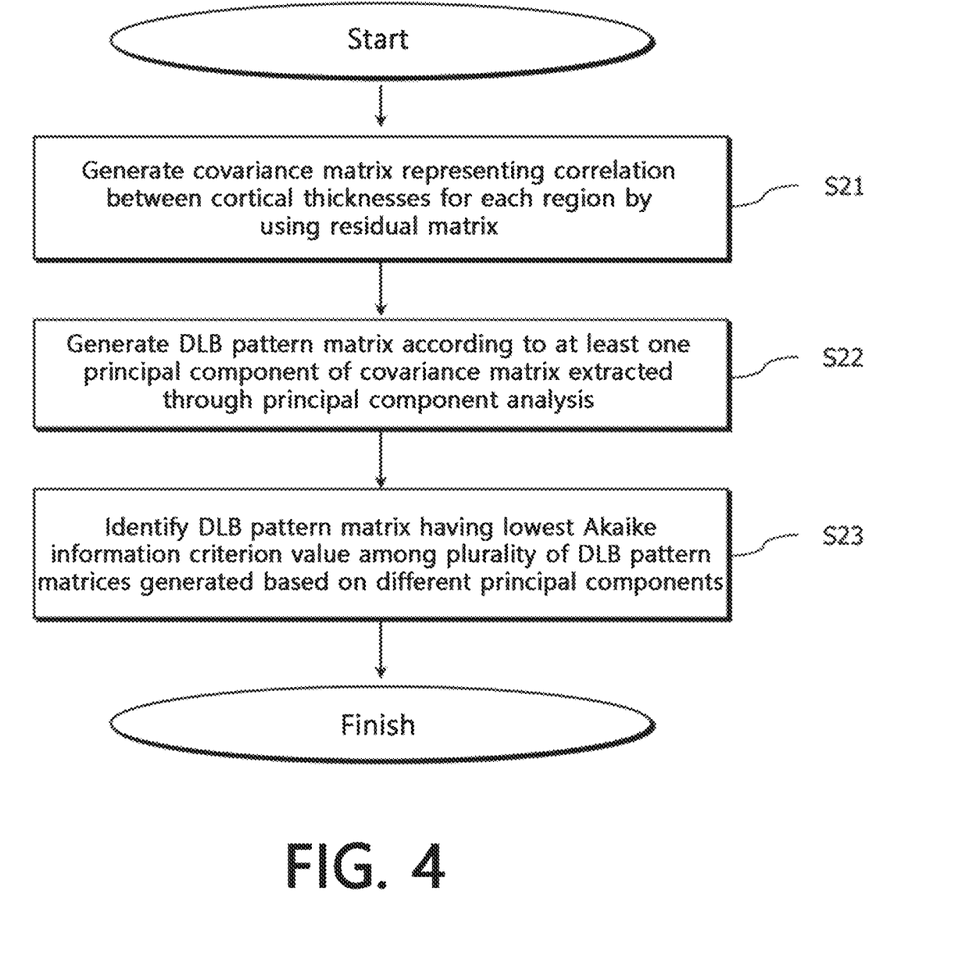
FIG. 4 is a diagram illustrating the operation flowchart of generating a DLB pattern matrix according to an exemplary embodiment of the present invention.

FIG. 4 is a diagram illustrating the operation flowchart of generating a DLB pattern matrix according to an exemplary embodiment of the present invention.

FIG. 4 describes an operation for explaining the DLB pattern matrix described in relation to S20 of FIG. 3.

According to an exemplary embodiment of the present invention, the processor 150 may generate a covariance matrix representing a correlation between cortical thicknesses for each region by using the residual matrix (S21).

The covariance matrix indicates how similar the fluctuations of each feature are, and it may indicate a correlation between cortical thicknesses for each region by using a residual matrix. More specifically, the covariance matrix may be obtained by dot product of the residual matrix.

According to an exemplary embodiment of the present invention, the processor 150 may generate a DLB pattern matrix according to at least one principal component (PC) of the covariance matrix that is extracted through principal component analysis (PCA) (S22).

Principal component analysis is an analysis that dimensionally reduces high-dimensional data to low-dimensional data while preserving the variance of the data as much as possible, and it means Scaled Subprofile Model-Principal Component Analysis (SSM-PCA).

The processor 150 may extract at least one principal component of the covariance matrix through the principal component analysis.

If a plurality of eigenvectors that are capable of orthogonally projecting data are arranged in the order of large eigenvalues, principal components may be obtained in order of importance as a result. Principal component analysis algorithms used in this process may include previously published algorithms that have been analyzed with positron emission tomography (PET) data.

However, since performance of the DLB pattern matrix may vary depending on the combination of principal components, the processor 150 may generate the DLB pattern matrix by combining at least one extracted principal component. That is, the processor 150 may identify an optimal principal component combination that is capable of best differentiating the normal group from the patient group by using the extracted principal components so as to create an optimal model.

More specifically, the processor 150 may identify a DLB pattern matrix having the lowest Akaike information criterion (AIC) value among a plurality of DLB pattern matrices that are generated based on different principal components (S23).

AIC is a criterion for evaluating the relative quality of statistical models for a given data set, and when the AIC value is low, the relative quality of the statistical model is considered to be high.

Therefore, in the present invention, the DLB pattern matrix having the lowest AIC value is used as the DLB pattern matrix for determining the disease of the subject according to the present invention.

According to an exemplary embodiment of the present invention, by identifying a spatial covariance pattern of cortical thickness associated with dementia with Lewy bodies, it is possible to more quantitatively detect structural changes in the brain in the relationship between brain regions.

According to an exemplary embodiment of the present invention, the DLB pattern may be used as a biomarker by prioritizing objectivity and reproducibility while considering individual differences in the brain in an anatomical space.

Figure 5:
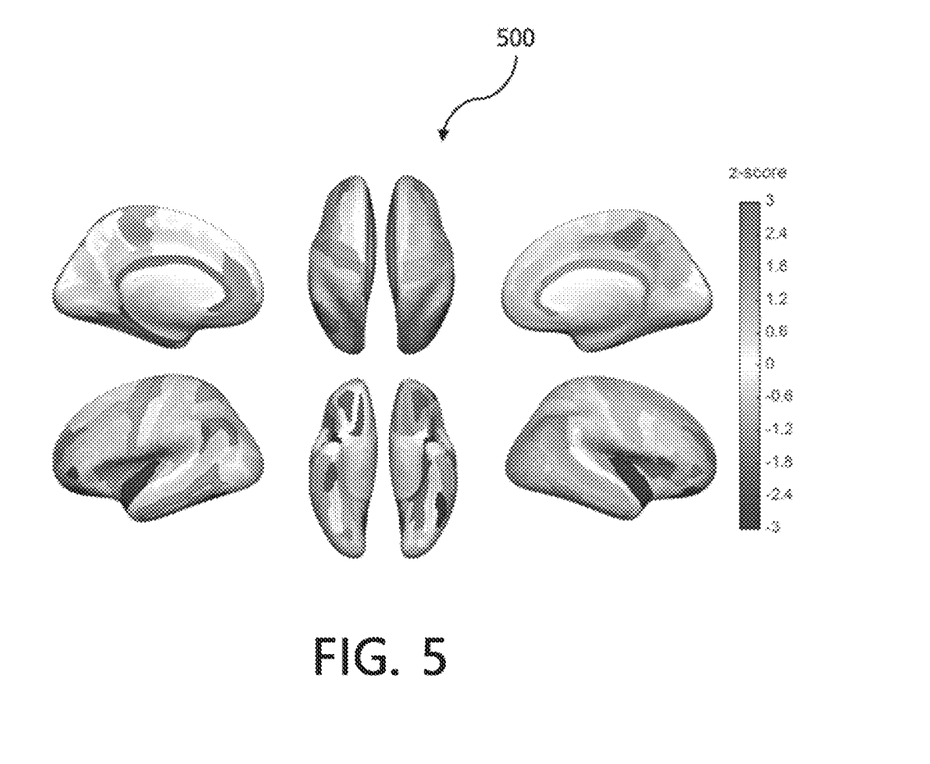
FIG. 5 is a diagram illustrating a DLB pattern according to an exemplary embodiment of the present invention.

FIG. 5 is a diagram illustrating a DLB pattern according to an exemplary embodiment of the present invention.

FIG. 5 shows a DLB pattern 500 in which the DLB pattern matrix described above in FIGS. 3 and 4 is standardized for each brain region and displayed.

It can be seen that the atrophy of cortical thicknesses in the prefrontal, middle temporal, insular cortex and occipital cortex is associated with higher metabolic pattern scores.

According to an exemplary embodiment of the present invention, the DLB pattern may be used for differential diagnosis and early diagnosis of dementia with Lewy bodies, and in patients with prodromal-stage Lewy body disease, it may be used to predict by differentiating future progression to dementia with Lewy bodies from progression to Parkinson's disease.

Accordingly, the present invention provides a method for diagnosing dementia with Lewy bodies (DLB) or predicting morbidity to DLB that is performed by the above-described device.

As used herein, the term "diagnosis" means to confirm the presence or characteristics of a pathological state, and for the purpose of the present invention, it means to confirm the presence or clinical symptoms of DLB in a subject to confirm whether the subject has developed DLB.

As used herein, the term "prediction" means to guess in advance about medical abduction, and for the purpose of the present invention, for patients in the prodromal stage of dementia, for example, patients with REM sleep behavior disorder who mostly progress to DLB or Parkinson's disease, it means to guess in advance whether the patients will be afflicted with DLB or Parkinson's disease.

The method for diagnosing DLB or predicting morbidity to DLB according to the present invention may be applied without limitation to any subject for whom DLB onset is to be confirmed. For example, the subject includes a normal group, an asymptomatic patient group in which the symptoms of dementia are not expressed or appear not to be expressed, and a patient group in a prodromal stage of dementia such as REM sleep behavior disorder or mild cognitive impairment, but the present invention is not limited thereto. In particular, when the subject is a patient group in the prodromal stage of dementia, it is possible to predict morbidity to DLB of the subject by applying the DLB pattern score according to the present invention.

Figure 6:
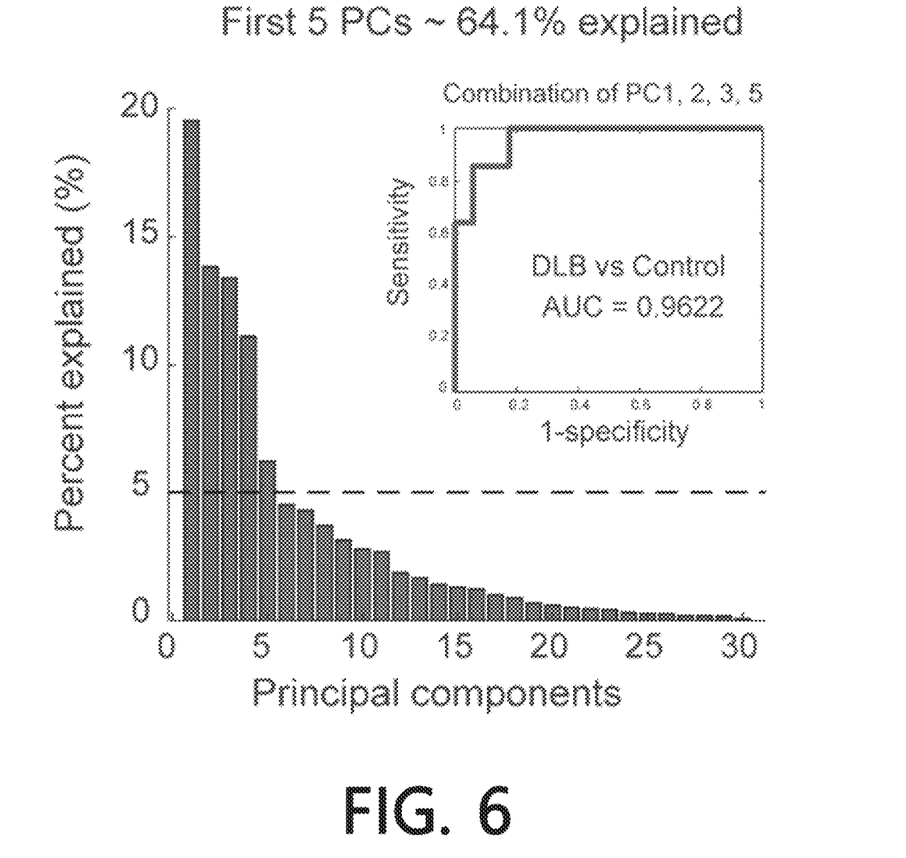
FIG. 6 is a graph showing the differential diagnosis sensitivity and specificity of a patient with dementia with Lewy bodies compared to a normal group, when the DLB pattern extracted in the present invention is applied clinically.

FIG. 6 shows the differential diagnosis sensitivity and specificity of a DLB patient compared to a normal group, when the DLB pattern extracted through the above-described process is applied to actual clinical practice.

As a result of analyzing the differential diagnosis and reflection of clinical characteristics by applying the DLB pattern according to an exemplary embodiment of the present invention to the DLB patient and the normal group, as shown in FIG. 6, it shows high differentiation between the normal group and the patient (AUC=0.962), and thus, it was confirmed that the presence of DLB in the subject could be accurately diagnosed with high specificity and sensitivity.

Furthermore, since the DLB pattern score showed a significant correlation with the Trail making test that is associated with frontal executive function abnormality, which is a characteristic of cognitive function abnormality in DLB patients, and the Rey complex figure test that is associated with spatial cognitive function abnormality, it was confirmed that it is an indicator that significantly reflects changes in cognitive function in patients with DLB.

Accordingly, the method for diagnosing DLB or predicting morbidity to DLB according to the present invention may diagnose DLB of a subject by additionally referring to various known test results for measuring changes in the cognitive function of DLB patients.

In another exemplary embodiment of the present invention, the DLB pattern extracted by the above-described process was applied to a patient with REM sleep behavior disorder corresponding to the prodromal stage of dementia with Lewy bodies to confirm changes in DLB patterns according to longitudinal observation and the accuracy of disease-specific morbidity prediction, thereby verifying the effects of the present invention were verified. As a result, when exceeding the standard score of the baseline DLB pattern score of 1 point was set as a cut-off, the sensitivity for future morbidity to DLB was measured at 80%, the specificity was measured at 100%, and the diagnostic accuracy was measured at 92.9%. Therefore, when the cutoff value of the DLB pattern standard score is 1, it is possible to accurately predict morbidity to DLB in patients with REM sleep behavior disorder with excellent sensitivity and specificity.

Meanwhile, when the standard score of the DLB pattern score of the subject is 1 point or less, it can be predicted that the subject is afflicted with Parkinson's disease.

In particular, based on the DLB pattern score within 4 years from the time point of conversion to DLB or Parkinson's disease, the sensitivity, specificity and diagnostic accuracy were all measured at 100%, and thus, it was confirmed that it is possible to accurately predict by differentiate whether patients with REM sleep behavior disorder will be afflicted with DLB or Parkinson's disease with more excellent sensitivity and specificity.

Therefore, since it is possible to differentiate and predict whether a patient with REM sleep behavior disorder will be afflicted with DLB or Parkinson's disease through the method for diagnosing DLB or predicting morbidity to DLB according to the present invention, a treatment strategy for each patient may be established based on the prediction results.

Furthermore, since the DLB pattern score showed a significant correlation with the immediate recall test associated with the memory of patients with REM sleep behavior disorder and the Rey complex figure test associated with spatial cognitive dysfunction, it was confirmed that it is an indicator that significantly reflects changes in the cognitive function of patients with REM sleep behavior disorder, and thus, as the DLB pattern score according to the present invention is applied to confirm whether the memory and spatial perception of patients with REM sleep behavior disorder are reduced, it is possible to monitor changes in the cognitive function of patients with REM sleep behavior disorder.

Accordingly, the method for diagnosing DLB or predicting morbidity to DLB according to the present invention may predict whether a subject is afflicted with DLB by additionally referring to various well-known test results for measuring changes in the cognitive function of patients with REM sleep behavior disorder.

The method for diagnosing DLB or predicting morbidity to DLB according to the present invention may diagnose DLB or predict morbidity to DLB of a subject by combining a known biomarker utilized for diagnosing DLB. The known biomarker may be at least one selected from the group consisting of clinical biomarkers, imaging biomarkers and blood biomarkers, but the present invention is not limited thereto.

For example, for the known clinical biomarkers, fluctuating cognitive function, repetitive and vivid hallucinations, REM sleep behavior disorder, Parkinsonian motor symptoms, balance disorder and repetitive falls, syncope, hyposmia, hypersomnia, severe autonomic nervous system symptoms, hypersensitivity to antipsychotics, other unexplained hallucinations, delirium, apathy, anxiety and depressive symptoms may be used, but the present invention is not limited thereto.

For the imaging biomarkers, decreased basal ganglia uptake on dopamine transporter functional imaging, decreased myocardial uptake of meta-iodobenzylguanidine (MIBG), posterior slow wave on quantitative EEG, reduced metabolism in the occipital lobe on fluorodeoxyglucose-positron emission tomography (FDG-PET) and insular atrophy on MRI may be used, but the present invention is not limited thereto.

Hereinafter, the present invention will be described in more detail through examples. However, the present invention can be made with various changes and can have various forms, and the specific examples and descriptions described below are only intended to help the understanding of the present invention, and are not intended to limit the present invention to specific disclosed forms. It should be understood that the scope of the present invention includes all modifications, equivalents and substitutes included in the spirit and technical scope of the present invention.

Example 1

Differential Diagnosis of Clinical Dementia with Lewy Bodies to which DLB Pattern Score is Applied 1-1. Data Collection In April 2021, approval for this prospective study was obtained from the IRB of Boramae Hospital operated by Seoul National University Hospital, and consent was obtained for a DLB patient group (n=22) and a normal group (n=44) recruited from Boramae Hospital operated by Seoul National University Hospital, and afterwards, the reflection of differential diagnosis and clinical characteristics was analyzed by applying the DLB pattern extracted in the present invention.

Table 1 shows the clinical information of the DLB patient and normal groups. Each item was presented as mean±standard deviation except for number and male/female.

TABLE 1

|  | Healthy control group (normal group) | DLB |
| --- | --- | --- |
| Number | 44 | 22 |
| Male/female | 15/29 | 13/8 |
| Age | 68.6 ± 6.3 | 76.1 ± 5.9 |
| Mini-Mental State Examination (MMSE) | 27.7 ± 2.1 | 18.7 ± 5.3 |
| Digit Span Test | −0.48 ± 0.68 | −0.29 ± 1.41 |
| Trail Making Test-A (TMT-A) | −0.097 ± 0.39 | −1.22 ± 1.99 |
| Color Word Stroop Test (CWST) | −0.21 ± 0.90 | −1.45 ± 1.29 |
| Boston Name Test (BNT) | 0.67 ± 0.45 | −1.60 ± 0.89 |
| Ray Complex Figure Test (RCFT) | −0.98 ± 1.16 | −2.49 ± 1.47 |
| Seoul Verbal Learning Test-Immediate Recall (SVLTi) | 0.43 ± 1.02 | −1.25 ± 0.86 |
| Seoul Verbal Learning Test-Delayed Recall (SVLTd) | 0.37 ± 0.93 | −1.33 ± 1.16 |
| Seoul Verbal Learning Test-Recognition (SVLTr) | 0.77 ± 0.68 | −1.25 ± 1.24 |
| Controlled Oral Word Association Test (COWAT) | −0.083 ± 0.81 | −1.07 ± 1.65 |
| Trail Making Test-B (TMT-B) | 0.54 ± 0.20 | −4.00 ± 2.66 |

1-2. Differential Diagnosis of Dementia with Lewy Bodies to which the DLB Pattern Score is Applied As a result of applying the DLB pattern extracted in the present invention to the normal group and DLB patients in which the age and gender were matched, when the standard score of 1 was set as a cut-off, high differentiation (AUC=0.962) was shown between the normal group and the Lewy body dementia patient group, as confirmed in FIG. 6.

1-3. Confirmation of Association with Specific Cognitive Function Abnormality Specific to Dementia with Lewy Bodies to which the DLB Pattern Score is Applied In order to confirm whether the DLB pattern extracted in the present invention reflects cognitive function abnormality that is specific to dementia with Lewy bodies, an integrated neuropsychological test (SNSB-II) was performed on DLB patients, and this test included a mini-mental state examination (MMSE), a digit span test, a Korean color word Stroop test, trail making tests (TMT-A and -B), a controlled oral word association test, a Seoul verbal learning test, a Rey complex figure test and a Korean Boston naming test.

As confirmed in Table 2, the DLB pattern scores showed a significant correlation with the trail making test that is associated with the Frontal executive function abnormality, which is a characteristic of cognitive function abnormality in patients with dementia with Lewy bodies, and the Rey complex figure test that is associated with spatial cognitive function abnormality.

TABLE 2

| Cognitive Test | Correlation coefficient | P value |
| --- | --- | --- |
| Mini-Mental State Examination (MMSE) | −0.31 | 0.035 |
| Digit Span Test | −0.11 | 0.58 |
| Trail Making Test-A (TMT-A) | −0.55 | 0.024 |
| Color Word Stroop Test (CWST) | −0.24 | 0.32 |
| Boston Name Test (BNT) | −0.35 | 0.062 |
| Ray Complex Figure Test (RCFT) | −0.54 | 0.0047 |
| Seoul Verbal Learning Test-Immediate Recall (SVLTi) | −0.11 | 0.56 |
| Seoul Verbal Learning Test-Delayed Recall (SVLTd) | −0.25 | 0.18 |
| Seoul Verbal Learning Test-Recognition (SVLTr) | −0.16 | 0.41 |
| Controlled Oral Word Association Test (COWAT) | 0.083 | 0.73 |
| Trail Making Test-B (TMT-B) | −0.56 | 0.036 |

Based on the above test results, it was confirmed that the DLB pattern extracted in the present invention is an indicator that significantly reflects the cognitive function changes corresponding to DLB.

Example 2

Verification of Disease-Specific Morbidity Prediction for Prodromal-Stage Patients to which the DLB Pattern Score is Applied 2-1. Data Collection After obtaining approval for this prospective study from the IRB of Seoul National University Hospital in July 2013, consent was obtained from a patient group (n=50) with REM sleep behavior disorder recruited from Boramae Hospital operated by Seoul National University Hospital, and afterwards, the morbidity of patients with REM sleep behavior disorder to dementia with Lewy bodies and Parkinson's disease was observed with longitudinal follow-up for up to 8 years. In this study, baseline brain imaging (MRI) was taken for patients with REM sleep behavior disorder at the time of recruitment, and follow-up brain imaging (MRI) was taken 2 years and 4 years after recruitment, respectively.

Table 3 shows the clinical information of the DLB patients. Each item was presented as mean±standard deviation except for number and male/female.

TABLE 3

| | REM sleep behavior disorder |
|---|---|
| Number | 50 |
| Male/female | 27/23 |
| Age | 70.6 ± 5.9 |
| REM Sleep Morbidity Period | 5.0 ± 4.7 |
| Mini-Mental State Examination (MMSE) | 27.0 ± 2.6 |
| Olfactory Function Test (B-SIT) | 6.2 ± 2.8 |
| Digit Span Test | 0.11 ± 0.90 |
| Trail Making Test-A (TMT-A) | −0.32 ± 1.01 |
| Color Word Stroop Test (CWST) | −0.77 ± 1.22 |
| Boston Name Test (BNT) | −0.16 ± 1.17 |
| Ray Complex Figure Test (RCFT) | −1.44 ± 1.52 |
| Seoul Verbal Learning Test-Immediate Recall (SVLTi) | −0.31 ± 0.97 |
| Seoul Verbal Learning Test-Delayed Recall (SVLTd) | −0.62 ± 1.12 |
| Seoul Verbal Learning Test-Recognition (SVLTr) | −0.21 ± 1.14 |
| Controlled Oral Word Association Test (COWAT) | −0.56 ± 1.01 |
| Trail Making Test-B (TMT-B) | −1.49 ± 2.47 |

Figure 7:
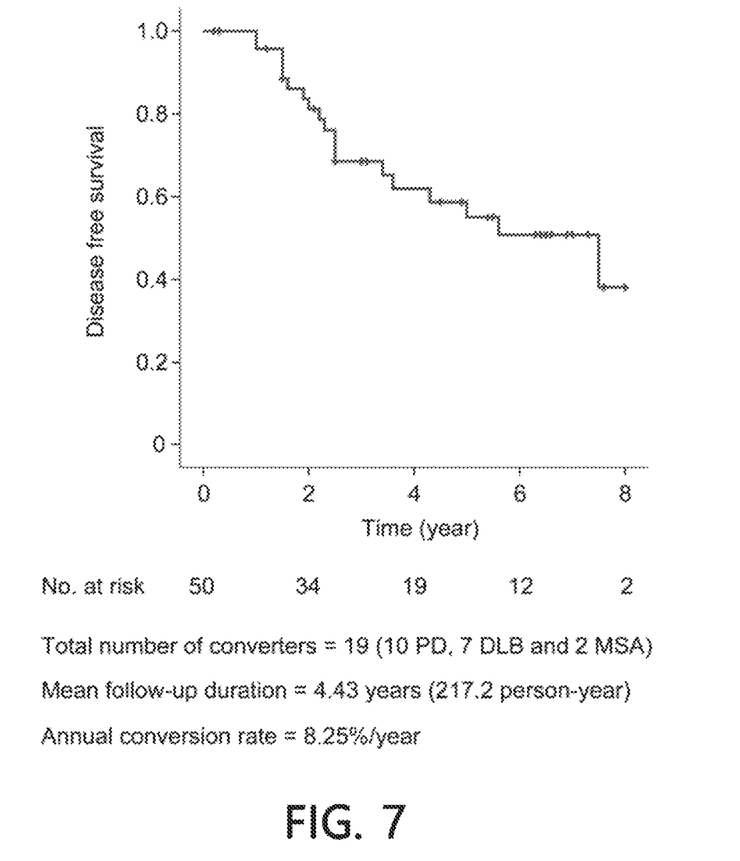
FIG. 7 shows the trend of disease morbidity during the follow-up period of patients with prodromal-stage DLB by the Kaplan Meier survival curve.

During an average of 4.43 years of longitudinal follow-up, a total of 10 patients in the REM sleep behavior disorder patient group were afflicted with degenerative brain disease, 10 were converted to Parkinson's disease, and 7 were converted to dementia with Lewy bodies (2 were afflicted as multiple system atrophy patients). The trend of disease morbidity during the follow-up period is represented by the Kaplan Meier survival curve in FIG. 7.

2-2. Prediction of Morbidity to Dementia with Lewy Bodies to which the DLB Pattern Score is Applied When exceeding the standard score of the 8-base DLB pattern score of 1 point was set as a cut-off, the sensitivity for predicting future morbidity to DLB among the diseased group was measured at 85.7%, the specificity was measured at 90%, and the diagnostic accuracy was measured at 88.2%. These results are shown in Table 4 in comparison with the predictive power of clinical biomarkers and imaging biomarkers for existing REM sleep behavior disorder and DLB. based on the DLB pattern scores within 4 years from the time of transition to the disease.

TABLE 4

| | Differentiation prediction for Parkinson's disease and dementia with Lewy bodies Differentiation | | |
|---|---|---|---|
| | Sensitivity | Specificity | Diagnostic accuracy |
| DLB pattern | 85.7 | 90 | 88.2 |
| Average cortical thickness | 85.7 | 0 | 35.3 |
| Dopamine transporter imaging | 57.1 | 10 | 29.4 |
| Mild cognitive impairment | 85.7 | 40 | 31.3 |
| Loss of smell | 66.7 | 33.3 | 31.3 |
| Motor function impairment | 85.7 | 30 | 58.2 |

2-3. Confirmation of Association with REM Sleep Behavior Disorder and Cognitive Dysfunction to which the DLB Pattern Score is Applied Based on the results of the baseline and follow-up (tests performed 2 years and 4 years from the time of recruitment) cognitive function tests performed on the patients with REM sleep behavior disorder in Example 2-2 above, an analysis was conducted to determine if there is a correlation between the DLB pattern scores, the underlying cognitive function and changes in the cognitive function that progressed over 4 years. This test included a mini-mental state examination (MMSE), a digit span test, a Korean color word Stroop test, trail making tests (TMT-A and -B), a controlled oral word association test, a Seoul verbal learning test, a Rey complex figure test and a Korean Boston naming test.

As a result, as confirmed in Table 5, the DLB pattern scores showed a significant correlation with the digit span test, which reflects the executive function of the frontal lobe among the basic cognitive functions of patients with REM sleep behavior disorder. In addition, the DLB pattern scores showed a significant correlation with changes over 4 years in the memory (immediate recall test) and spatial perception ability (Rey complex figure test) of patients with REM sleep behavior disorder.

TABLE 5

| | Baseline evaluation | | Changes over 4 years | |
|---|---|---|---|---|
| | Correlation coefficient | P value | Correlation coefficient | P value |
| Digit Span Test | −0.32 | 0.033 | 0.29 | 0.61 |
| Trail Making Test-A (TMT-A) | −0.21 | 0.21 | 0.13 | 0.067 |
| Color Word Stroop Test (CWST) | 0.31 | 0.075 | −0.43 | 0.31 |
| Boston Name Test (BNT) | 0.042 | 0.79 | −0.23 | 0.37 |
| Ray Complex Figure Test (RCFT) | −0.067 | 0.68 | −0.22 | 0.035 |
| Seoul Verbal Learning Test-Immediate Recall (SVLTi) | 0.073 | 0.65 | −0.46 | 0.018 |
| Seoul Verbal Learning Test-Delayed Recall (SVLTd) | 0.061 | 0.7 | −0.51 | 0.068 |
| Seoul Verbal Learning Test-Recognition (SVLTr) | −0.073 | 0.64 | −0.41 | 0.54 |
| Controlled Oral Word Association Test (COWAT) | 0.067 | 0.68 | −0.16 | 0.54 |
| Trail Making Test-B (TMT-B) | 0.25 | 0.13 | −0.002 | 0.99 |

As confirmed in Table 4, when comprehensively considering the predictive sensitivity, specificity and diagnostic accuracy of the biomarkers, the predictive power utilizing the DLB pattern score was significantly superior to existing clinical biomarkers and imaging biomarkers. The sensitivity, specificity and diagnostic accuracy were all measured at 100%

Since patients with REM sleep behavior disorder progressing to DLB show memory decline compared to patients with REM sleep behavior disorder clinically progressing to Parkinson's disease, it was confirmed that the DLB pattern extracted in the present invention is an indicator that significantly reflects the cognitive function and changes thereof in patients with REM sleep behavior disorder, which corresponds to the prodromal stage of DLB.

EXPLANATION OF REFERENCE NUMERALS

100: Electronic device
110: Input device
120: Communicator
130: Display
140: Memory
150: Processor

The invention claimed is:

1. An electronic device for diagnosing dementia with Lewy bodies (DLB) or predicting morbidity to DLB, comprising:
a display;
a communicator configured to receive a first brain MRI image of a subject to be diagnosed, the first brain MRI image is a target brain MRI image;
a memory configured to store operating programs;
a processor configured to execute the programs to:
standardize and preprocess the first brain MRI image,
generate a first vector, the elements of the first vector corresponding to cortical thicknesses of predetermined regions, the cortical thicknesses being calculated using the first brain MRI image,
compute an inner product between the first vector and a second vector to generate a DLB pattern score, the second vector being a DLB pattern vector pre-stored in the memory,
diagnose the subject as having DLB or predict morbidity to DLB based on the DLB pattern score, and
display the result of the diagnosis on the display,
wherein the second vector is generated by:
measuring cortical thicknesses for the predetermined regions of the brain for second brain MRI images of a normal group and a DLB patient group,
generating a residual matrix, each element of the residual matrix being a difference between an average cortical thickness and the cortical thickness for each region in each of the second brain MRI image, and
calculating weights for each region of the brain, the weights reflecting relationships between brain regions, the elements of the second vector being the weights.

2. The electronic device of claim 1, wherein the processor is configured to generate a covariance matrix representing a correlation between the cortical thicknesses for the each region by using the residual matrix, and generate at least one DLB pattern vector according to at least one principal component of the covariance matrix extracted through principal component analysis.

3. The electronic device of claim 2, wherein the processor is further configured to select a DLB pattern vector as the second vector, the second vector having the lowest Akaike information criterion value among a plurality of DLB pattern vectors generated based on different principal components.

4. The electronic device of claim 1, wherein the processor is configured to calculate the DLB pattern score as a standard score compared to the distribution of DLB pattern scores in the normal group to diagnose the subject as DLB or predict morbidity to DLB.

5. The electronic device of claim 4, wherein age and gender of the normal group are matched by age and gender of the subject.

6. The electronic device of claim 4, wherein the processor is configured to differentiate the subject from Parkinson's disease to diagnose the subject as DLB or predict morbidity to DLB, based on whether a cut-off value of the standard score is exceeded.

7. The electronic device of claim 6, wherein the processor is configured to diagnose the subject as DLB or predict that the subject is afflicted with DLB, if the standard score is more than the cut-off value, and predict that the subject is afflicted with Parkinson's disease, if the standard score is less than or equal to the cut-off value.

8. The electronic device of claim 7, wherein the processor is configured to predict that the subject's memory and spatial perception ability are reduced, if the subject is a REM sleep behavior disorder patient and the standard score is more than the cut-off value.

9. The electronic device of claim 6, wherein the cut-off value is 1.

10. A method for diagnosing dementia with Lewy bodies (DLB) or predicting morbidity to DLB which is performed by a device for diagnosing DLB or predicting morbidity to DLB, the method comprising:
receiving a first brain MRI image of a subject to be diagnosed;
standardizing and preprocessing the first brain MRI image, the first brain MRI image is a target brain MRI image;
generating a first vector, the elements of the first vector corresponding to cortical thicknesses of predetermined regions, the cortical thicknesses being calculated using the first brain MRI image;
computing an inner product between the first vector and a second vector to generate a DLB pattern score, the second vector being a DLB pattern vector pre-stored in a memory;
diagnosing the subject as having DLB or predicting morbidity to DLB based on the DLB pattern score; and
displaying the result of the diagnosis;
wherein the second vector is generated by:
measuring cortical thicknesses for the predetermined regions of the brain for second brain MRI images of a normal group and a DLB patient group,
generating a residual matrix, each element of the residual matrix being a difference between an average cortical thickness and the cortical thickness for each region in each of the second brain MRI image, and
calculating weights for each region of the brain, the weights reflecting relationships between brain regions, the elements of the second vector being the weights.

11. The method of claim 10, further comprising:
generating a covariance matrix representing a correlation between the cortical thicknesses for the each region by using the residual matrix; and
generating at least one DLB pattern vector according to at least one principal component of the covariance matrix extracted through principal component analysis.

12. The method of claim 11, further comprising:
selecting a DLB pattern vector as the second vector, the second vector having the lowest Akaike information criterion value among a plurality of DLB pattern vectors generated based on different principal components.

13. The method of claim 10, wherein the step of diagnosing the subject as DLB or predicting morbidity to DLB comprises:

diagnosing the subject as DLB or predicting morbidity to DLB by calculating the DLB pattern score as a standard score compared to the distribution of DLB pattern scores in the normal group.

14. The method of claim 13, wherein age and gender of the normal group are matched by age and gender of the subject.

15. The method of claim 13, wherein the step of diagnosing the subject as DLB or predicting morbidity to DLB comprises:
diagnosing the subject as DLB or predicting morbidity to DLB based on whether a cut-off value of the standard score is exceeded.

16. The method of claim 15, wherein the step of diagnosing the subject as DLB or predicting morbidity to DLB comprises:
diagnosing the subject as DLB or predicting that the subject is afflicted with DLB, if the standard score is more than the cut-off value; and
predicting that the subject is afflicted with Parkinson's disease, if the standard score is less than or equal to the cut-off value.

17. The method of claim 16, further comprising:
determining that the subject's memory and spatial perception ability are reduced, if the subject is a REM sleep behavior disorder patient and the standard score is more than the cut-off value.

18. The method of claim 15, wherein the cut-off value is 1.

19. The method of claim 10, further comprising:
combining with at least one selected from a group consisting of a clinical biomarker, an imaging biomarker and a blood biomarker of the subject to predict whether the subject has developed DLB or is afflicted with DLB.

* * * * *